(12) United States Patent
Gelb et al.

(10) Patent No.: US 11,396,499 B2
(45) Date of Patent: Jul. 26, 2022

(54) LYSOSOMAL ACID LIPASE ASSAY

(71) Applicant: University of Washington, Seattle, WA (US)

(72) Inventors: Michael H. Gelb, Seattle, WA (US); Sophia M. B. Masi, Seattle, WA (US)

(73) Assignee: University of Washington, Seattle, WA (US)

( * ) Notice: Subject to any disclaimer, the term of this patent is extended or adjusted under 35 U.S.C. 154(b) by 286 days.

(21) Appl. No.: 16/711,214

(22) Filed: Dec. 11, 2019

(65) Prior Publication Data

US 2020/0190050 A1 Jun. 18, 2020

Related U.S. Application Data

(60) Provisional application No. 62/778,830, filed on Dec. 12, 2018.

(51) Int. Cl.
| | | |
|---|---|---|
| *C07D 311/16* | (2006.01) | |
| *C12Q 1/25* | (2006.01) | |
| *C12Q 1/34* | (2006.01) | |
| *G01N 33/52* | (2006.01) | |
| *G01N 33/68* | (2006.01) | |
| *A61K 45/06* | (2006.01) | |

(52) U.S. Cl.
CPC .......... *C07D 311/16* (2013.01); *G01N 33/52* (2013.01); *G01N 33/6848* (2013.01); *A61K 45/06* (2013.01)

(58) Field of Classification Search
CPC .......... C07D 311/16; C12Q 1/25; C12Q 1/34
See application file for complete search history.

(56) References Cited

U.S. PATENT DOCUMENTS

| | | | |
|---|---|---|---|
| 8,663,631 | B2 | 3/2014 | Quinn |
| 10,221,441 | B1 | 3/2019 | Wood et al. |
| 2003/0059420 | A1 | 3/2003 | Grabowski et al. |
| 2012/0298885 | A1 | 11/2012 | Ikami et al. |
| 2017/0023583 | A1 | 1/2017 | Ornatsky |
| 2017/0219566 | A1 | 8/2017 | Chhajlani |
| 2019/0144916 | A1 | 5/2019 | Gelb et al. |

FOREIGN PATENT DOCUMENTS

| | | |
|---|---|---|
| CN | 106573153 A | 4/2017 |
| EP | 2 700 717 B1 | 6/2016 |
| EP | 3 284 469 A2 | 2/2018 |
| GR | 1007801 B | 1/2013 |
| RU | 2017144777 A | 6/2019 |
| WO | 2012/027612 A1 | 3/2012 |
| WO | 2015/061738 A1 | 4/2015 |

OTHER PUBLICATIONS

Jacks et al. (Analytical Biochemistry (1967), 21(2), 279-85). Abstarct.*
Aguisanda, F., et al., "Targeting Wolman disease and cholesterol ester storage disease: disease pathogenesis and therapeutic development," Current Chemical Genomics and Translational Medicine 11:1-18, 2017.
Brown, W.J., et al., "Use of Nile red stain in the detection of cholesteryl ester accumulation in acid lipase-deficient fibroblasts," Archives of Pathology & Laboratory Medicine 112(3):295-297, Mar. 1988.
Camarena, C., et al. , "Update on lysosomal acid lipase deficiency: Diagnosis, treatment and patient management," Medicina Clínica (English Edition) 148(9):429.e1-429.e10, May 2017.
Canaan, S., et al., "Gastric lipase: Crystal structure and activity," Biochimica et Biophysica Acta 1441:197-204, 1999.
Dairaku, T., et al., "A practical fluorometric assay method to measure lysosomal acid lipase activity in dried blood spots for the screening of cholesteryl ester storage disease and Wolman disease," Molecular Genetics and Metabolism 111(2):193-196, 2014.
Ebdrup, S., et al., "Synthesis and structure—activity relationship for a novel class of potent and selective carbamate-based inhibitors of hormone selective lipase with acute in vivo antilipolytic effects," Journal of Medicinal Chemistry 50:5449-5456, 2007.
Elliot, S., et al., "Pilot study of newborn screening for six lysosomal storage diseases using Tandem Mass Spectrometry," Molecular Genetics and Metabolism 118:304-309, 2016.
Gelb, M.H., et al., "Newborn Screening for Lysosomal Storage Disorders: Methodologies for Measurement of Enzymatic Activities in Dried Blood Spots," International Journal of Neonatal Screening 5(1), 2019, 12 pages.
Giugliani, R., et al., "Current molecular genetics strategies for the diagnosis of lysosomal storage disorders," Expert Review of Molecular Diagnostics 16(1):113-123, 2016.
Gravel, R.A., et al., "The GM2 Gangliosidoses," in Scriver, C.R., et al. (eds.), "The Metabolic and Molecular Bases of Inherited Disease," 8th ed., New York: McGraw-Hill, 2001, pp. 3827-3874.
Hamilton, J., et al., "A new method for the measurement of lysosomal acid lipase in dried blood spots using the inhibitor Lalistat 2," Clinica Chimica Acta 413:1207-1210, 2012.
Harlan, F.K., et al., "Fluorogenic Substrate for Visualizing Acidic Organelle Enzyme Activities," PLOS One 11(5):e0156312, 2016, 19 pages.
Hoffman, E.P., et al., "Lysosomal Acid Lipase Deficiency," in Adam, M.P., et al. (eds.), "GeneReviews® [Internet]," University of Washington, Seattle; rev. Sep. 2016, 17 pages.
Jones, S.A., et al., "Survival in infants treated with sebelipase Alfa for lysosomal acid lipase deficiency: An open-label, multicenter, dose-escalation study," Orphanet Journal of Rare Diseases 12:25, 2017, 11 pages.
Kumar, A.B., et al., "Tandem Mass Spectrometry Has a Larger Analytical Range than Fluorescence Assays of Lysosomal Enzymes: Application to Newborn Screening and Diagnosis of Mucopolysaccharidoses Types II, IVA, and VI," Clinical Chemistry 61(11):1363-1371, 2015.

(Continued)

*Primary Examiner* — Bruck Kifle
(74) *Attorney, Agent, or Firm* — Christensen O'Connor Johnson Kindness PLLC

(57) ABSTRACT

Lysosomal acid lipase (LAL) substrates, assays for lysosomal acid lipase using the substrates, and methods for diagnosing diseases and conditions attributable to lysosomal acid lipase deficiency.

20 Claims, 4 Drawing Sheets

(56) References Cited

OTHER PUBLICATIONS

Li, Y., et al., "Direct multiplex assay of lysosomal enzymes in dried blood spots for newborn screening," Clinical Chemistry 50(10):1785-1796, 2004.
Lukacs, Z., et al., "Best practice in the measurement and interpretation of lysosomal acid lipase in dried blood spots using the inhibitor Lalistat 2," Clinica Chimica Acta 471:201-205, Aug. 2017.
Masi, S., et al., "Specific Substrate for the Assay of Lysosomal Acid Lipase," Clinical Chemistry 64(4):690-696, Apr. 2018.
Nègre, A., "New spectrophotometric assays of acid lipase and their use in the diagnosis of Wolman and cholesteryl ester storage diseases," Analytical Biochemistry 145:398-405, 1985.
Porto, A.F., "Lysosomal acid lipase deficiency: Diagnosis and treatment of Wolman and Cholesteryl Ester Storage Diseases," Pediatric Endocrinology Reviews 12(Suppl 1):125-132, Sep. 2014.
Rajamohan, F., et al., "Expression and functional characterization of human lysosomal acid lipase gene (LIPA) mutation responsible for cholesteryl ester storage disease (CESD) phenotype," Protein Expression and Purification 110:22-29, 2015.
Reiner, Z., et al., "Lysosomal acid lipase deficiency—An under-recognized cause of dyslipidaemia and liver dysfunction," Atherosclerosis 235(1):21-30, 2014.
Reynolds, T., "Cholesteryl ester storage disease: A rare and possibly treatable cause of premature vascular disease and cirrhosis," Journal of Clinical Pathology 66(11):918-923, 2013.
Voorink-Moreta, M., et al., "Rapid screening for lipid storage disorders using biochemical markers. Expert center data and review of the literature," Molecular Genetics and Metabolism 123(2):76-84, Feb. 2018.
Wolfe, B.J., et al., "Tandem mass spectrometry for the direct assay of lysosomal enzymes in dried blood spots: Application to screening newborns for mucopolysaccharidosis II (Hunter Syndrome)," Analytical Chemistry 83:1152-1156, 2011.
Yu, C., et al., "Enzymatic Screening and Diagnosis of Lysosomal Storage Diseases," North American Journal of Medicine & Science 6(4):186-193, 2013. (Author Manuscript provided, PMCID: PMC4902264, available in PMC Jun. 10, 2016, 15 pages.)

\* cited by examiner

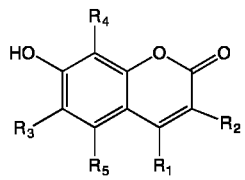

| Compound | Groups[1] | Commercial Source |
|---|---|---|
| 1 | $R_1$ = n-Propyl, $R_4$ = Me | ChemBridge |
| 14 | $R_1$ = Me, $R_2$ = Cl | Sigma |
| 15 | $R_1$ = Phenyl | Sigma |
| 16 | $R_1$ = $R_2$ = -(CH$_2$)$_5$- | Enamine |
| 17 | $R_1$ = 4-F-Phenyl | ArkPharm |
| 18 | $R_1$ = CH$_2$OMe | Matrix Scientific |
| 19 | $R_1$ CF$_3$, $R_3$ = Cl | Apollo Scientific Limited |
| 20 | $R_1$ = n-Butyl | ChemBridge |
| 21 | $R_1$ = n-Butyl, $R_4$ = Me | Oakwood Chemical |
| 22 | $R_1$ = Me, $R_3$ = Cl | Indofine |
| 23 | $R_1$ = $R_2$ = $R_3$ = Me | Sigma |
| 24 | $R_1$ = Me, $R_2$ = 2,4-Cl$_2$-Phenyl | Indofine |
| 25 | $R_1$ = N-CH$_2$-Morphilino | Matrix Scientific |
| 26 | $R_1$ = $R_2$ = -(CH$_2$)$_4$-, $R_3$ = Et | Oakwood Chemical |
| 27 | $R_1$ = Me, $R_2$ = Et | Matrix Scientific |
| 28 | $R_1$ = Me, $R_2$ = CH$_2$Phenyl | Sigma |
| 29 | $R_1$ = Me, $R_2$ = Me | Matrix Scientific |
| 30 | $R_1$ = Me, $R_3$ = Ethyl | Enamine |
| 31 | $R_2$ = Phenyl | Indofine |
| 32 | $R_1$ = Et, $R_4$ = Me | ChemBridge |
| 33 | $R_1$ = 4-Pyridyl | Matrix Scientific |
| 34 | $R_1$ = -CONH-(4-Pyridyl) | AK Scientific |
| 35 | $R_1$ = $R_2$ = -(CH$_2$)$_3$- | Sigma |
| 36 | $R_2$ = CN | Indofine |
| 37 | $R_1$ = Me, $R_2$ = Br | Key Organics |
| 4MU | $R_1$ = Me | Sigma |

[1] R groups not specified are H atoms.

*Fig. 5*

| Type | Sample | LAL Activity (μmol/hr/L blood) | Mean | CV |
|---|---|---|---|---|
| Children under 5 years | 1 | 101, 171, 116, 195, 146 | 145.9 | 23.6 |
| | 2 | 542, 581, 619, 642, 660 | 609.1 | 7.0 |
| | 3 | 310, 368, 406, 393, 346, 332 | 359.2 | 9.4 |
| | 4 | 301, 295, 276, 291, 306, 275 | 290.8 | 4.0 |
| | 5 | 580, 546, 527, 550, 554 | 551.3 | 3.0 |
| | 6 | 560, 713, 407, 584, 414, 628 | 551.1 | 20.0 |
| | 7 | 267, 244, 264, 241, 228, 224 | 244.9 | 6.6 |
| | 8 | 346 358, 400, 395, 344, 322 | 361.0 | 7.8 |
| | 9 | 556, 612, 584, 612, 582, 637 | 597.4 | 4.4 |
| | 10 | 140, 211, 159, 187, 105, 202 | 167.6 | 22.0 |
| | 11 | 158, 181, 237, 148, 286, 259 | 211.7 | 24.6 |
| | 12 | 933, 934, 1034, 790, 898, 698 | 881.1 | 12.4 |
| | 13 | 525, 544, 485, 508, 538, 440 | 506.8 | 7.0 |
| | 14 | 621, 581, 676, 671, 718, 722 | 665.1 | 7.6 |
| | 15 | 332, 530, 497, 506, 400, 487 | 458.6 | 15.2 |
| Adults | 1 | 598, 555, 653, 578, 608 | 598.5 | 5.5 |
| | 2 | 712, 701, 674, 632, 588, 636 | 657.1 | 6.5 |
| | 3 | 492, 499, 506, 480, 453, 465 | 482.2 | 3.9 |
| | 4 | 962, 842, 862, 848, 1016, 849 | 896.3 | 7.5 |
| | 5 | 846, 852, 852, 864, 923, 907 | 874.0 | 3.4 |
| | 6 | 990, 979, 1129, 1152, 929 | 1035.8 | 8.5 |
| | 7 | 613, 555, 488, 536, 514, 470 | 529.0 | 8.9 |
| | 8 | 567, 547, 435, 644, 564, 488 | 540.7 | 12.2 |
| | 9 | 316, 330, 220, 247, 292, 236 | 273.4 | 15.2 |
| | 10 | 938, 796, 818, 627, 1112, 740 | 838.3 | 18.3 |
| | 11 | 447, 526, 695, 595, 596, 684 | 590.4 | 14.6 |
| | 12 | 424, 534, 376, 496, 368, 385 | 430.4 | 14.7 |
| LALD Patients | 1 | 5, 6, 4, 3, 5 | 4.5 | 22.1 |
| | 2 | 15, 12, 10, 11, 13, 9 | 11.8 | 15.4 |
| | 3 | 1, 2, 0, 1, 2 | 1.4 | 53.3 |
| | 4 | 3, 1, 0, 1, 0 | 0.8 | 190.2 |
| | 5 | 25, 12, 11, 31, 37, 17 | 22.2 | 43.5 |
| | 6 | 8, 6, 7, 6,7 | 6.8 | 8.5 |
| Blank | | 6.3 - 24.9 (n = 56) | 15.0 | 36.4 |

[1]DBS samples were all blank corrected.

*Fig. 6*

LYSOSOMAL ACID LIPASE ASSAY

CROSS-REFERENCE TO RELATED APPLICATION

This application claims the benefit of U.S. Application No. 62/778,830, filed Dec. 12, 2018, expressly incorporated herein by reference in its entirety.

STATEMENT OF GOVERNMENT LICENSE RIGHTS

This invention was made with government support under Grant Nos. F30 DH081853 and R01 DK067859 awarded by the National Institutes of Health. The government has certain rights in the invention.

BACKGROUND OF THE INVENTION

Lysosomal acid lipase (LAL) deficiency is an autosomal recessive lysosomal storage disease with two distinct phenotypes: a severe infantile form known as Wolman disease and a milder, later-onset form referred to as cholesterol ester storage disease (*Curr Chem Genom Transl Med* 2017; 11:1-18). Both forms are caused by mutations in the LIPA4 gene that encodes for LAL, a low pH-active, serine lipase in the same family as gastric lipase (*Biochim Biophys Acta* 1999; 1441:197-204). Patients with Wolman disease show signs at birth or within the first few weeks of life of hepatosplenomegaly, adrenal calcification, and failure to thrive. Without treatment, this lysosomal storage disease is fatal within the first year. The presentation of cholesterol ester storage disease is more variable but typically presents in early adolescence with hypercholesterolemia and early development of atherosclerosis in major arteries. These affected persons typically succumb from fatal cardiac disease within the third decade of life, although there are reports of affected individuals living into their 60s or 70s. These clinical differences are thought to be because of the degree of residual LAL activity, with patients having cholesterol ester storage disease typically displaying 1% to 5% residual LAL activity and patients with Wolman disease displaying no detectable activity; more than 40 mutations in the LIPA gene have been reported (*Prot Expr Purif* 2015; 110:22-9).

LAL is detected in leukocytes or fibroblasts using radiometric, immunologic, or fluorescence assays (The metabolic and molecular bases of inherited disease. 8th Ed. New York (NY): McGraw-Hill; 2001. p. 3827-3387). Hamilton and colleagues recently developed a fluorometric assay to detect LAL in dried blood spots (DBS) (Hamilton et al., *Clin Chim Acta* 2012; 413:1207-10). The assay is based on the release of 4-methylumbelliferone from its ester with palmitic acid. However, the substrate is not specific for LAL, and the method requires two assays performed in parallel, the first in the presence of a LAL-specific covalent inactivator Lalistat-2. LAL activity is calculated from the difference in these 2 assays.

Recently, enzyme replacement therapy with recombinant LAL (sebelipase α) has been approved by the Food and Drug Administration for management of LAL deficiency (*Orphanet J Rare Disl* 2017; 12:25). As with many lysosomal storage diseases, initiation of treatment before the onset of irreversible symptoms may be advantageous. Thus, newborn screening for LAL deficiency may be warranted. However, given the rarity of LAL deficiency, newborn screening for this enzyme might be practical if it could be added in a multiplex fashion to an existing lysosomal storage disease newborn screening panel, if it could be done inexpensively, and if the number of follow-up samples was minimal.

A need exists for a substrate that is selective for LAL in DBS, thereby allowing the activity of this enzyme to be measured in a single incubation. The present invention fulfills this need and provides further related advantages.

SUMMARY OF THE INVENTION

The present invention provides lysosomal acid lipase (LAL) substrates, assays for lysosomal acid lipase using the substrates, and methods for diagnosing diseases and conditions attributable to lysosomal acid lipase deficiency.

In one aspect, the invention provides LAL substrates. In certain embodiments, the LAL substrate is a compound having formula (I):

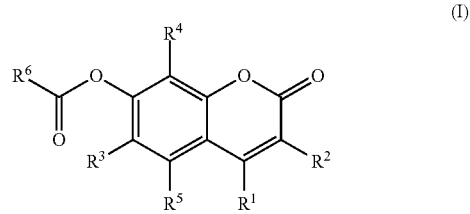

wherein
  $R^1$ is selected from the group consisting of
    (a) hydrogen,
    (b) linear or branched C1-C6 alkyl, optionally wherein one of the carbon atoms is replaced with an oxygen atom,
    (c) linear or branched C1-C6 haloalkyl,
    (d) phenyl optionally substituted with one or more halo groups or a phenyl group,
    (e) pyridyl,
    (f) C1-C3alkoxy C1-C3 alkyl, and
    (g) N—C1-C3alkyl morpholino;
  $R^2$ is selected from the group consisting of
    (a) hydrogen,
    (b) linear or branched C1-C6 alkyl, optionally wherein one of the carbon atoms is replaced with an oxygen atom,
    (c) halo,
    (d) CN, and
    (e) phenyl,
    (f) halo-substituted phenyl, and
    (g) benzyl,
    or $R^1$ and $R^2$ taken together with the carbon atoms to which they are attached form a 5-, 6-, or 7-membered ring;
  $R^3$ is selected from the group consisting of
    (a) hydrogen,
    (b) linear or branched C1-C6 alkyl, optionally wherein one of the carbon atoms is replaced with an oxygen atom,
    (c) halo;
  $R^4$ is selected from the group consisting of
    (a) hydrogen, and
    (b) linear or branched C1-C6 alkyl, optionally wherein one of the carbon atoms is replaced with an oxygen atom;
  $R^5$ is hydrogen; and
  $R^6$ is a linear or branched C5-C17 alkyl or alkenyl group, optionally wherein one, two, or three of the carbon atoms are replaced with an oxygen atom, wherein the alkenyl group includes one, two, three or four carbon-carbon double bonds, and wherein the alkyl or alkenyl group is optionally substituted with a phenyl group.

In certain of these embodiments, $R^1$ is hydrogen or linear C1-C6 alkyl, $R^2$ is hydrogen or linear C1-C6 alkyl, or $R^1$ and $R^2$ taken together with the carbon atoms to which they are attached form a 5-, 6-, or 7-membered ring, $R^3$ is hydrogen or linear C1-C6 alkyl, $R^4$ is hydrogen or linear C1-C6 alkyl, $R^5$ is hydrogen, and $R^6$ is —$(CH_2)_nCH_3$, wherein n is an integer from 5 to 17.

In other embodiments, the invention provides LAL substrates having formula (II):

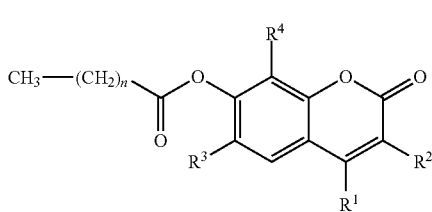

(II)

wherein
$R^1$ is selected from the group consisting of
(a) hydrogen,
(b) linear or branched C1-C6 alkyl,
(c) linear or branched C1-C6 haloalkyl,
(d) phenyl, and
(e) pyridyl;
$R^2$ is selected from the group consisting of
(a) hydrogen,
(b) linear or branched C1-C6 alkyl,
(c) benzyl,
(d) phenyl, and
(e) pyridyl,
or $R^1$ and $R^2$ taken together with the carbon atoms to which they are attached form a 5-, 6-, or 7-membered ring;
$R^3$ is selected from the group consisting of
(a) hydrogen,
(b) linear or branched C1-C6 alkyl,
(c) halo;
$R^4$ is hydrogen or linear or branched C1-C6 alkyl; and
n is an integer from 4 to 16.

In certain embodiments, the compounds of formula (II) are as follows:
$R^1$ is propyl, $R^2$ and $R^3$ are hydrogen, and $R^4$ is methyl;
$R^1$ is phenyl and $R^2$, $R^3$, and $R^4$ are hydrogen;
$R^1$ is trifluoromethyl, $R^2$ is hydrogen, $R^3$ is chloro, and $R^4$ is hydrogen;
$R^1$ is butyl (e.g., n-butyl) and $R^2$, $R^3$, and $R^4$ are hydrogen;
$R^1$ is methyl, $R^2$ is hydrogen, $R^3$ is chloro, and $R^4$ is hydrogen;
$R^1$ and $R^2$ taken together with the carbons to which they are attached form a 6-membered ring, $R^3$ is ethyl, and $R^4$ is hydrogen;
$R^1$ is methyl, $R^2$ is ethyl, and $R^3$ and $R^4$ are hydrogen;
$R^1$, $R^3$, and $R^4$ are hydrogen and $R^2$ is phenyl;
$R^1$ is ethyl, $R^2$ and $R^3$ are hydrogen, and $R^4$ is methyl; and
$R^1$ is pyridyl and $R^2$, $R^3$, and $R^4$ are hydrogen.

In certain of these embodiments, n is 14.

In one embodiment, the LAL substrate is the palmitoyl ester of 4-propyl-8-methyl-7-hydroxycoumarin(4-propyl-8-methyl-7-palmitoyloxycoumarin) (P-PMHC).

In another embodiment, the LAL substrate is the palmitoyl ester of 3-ethyl-4-methyl-7-hydroxycoumarin(3-ethyl-4-methyl-7-palmitoyloxycoumarin).

In a further embodiment, the LAL substrate is a compound of formula (II) wherein $R^1$ and $R^2$ taken together with the carbons to which they are attached form a 6-membered ring, $R^3$ is ethyl, $R^4$ is hydrogen, and n is 14.

In another aspect of the invention, LAL assays are provided.

In certain embodiments, the invention provides methods for assaying lysosomal acid lipase, comprising:
(a) incubating a sample with a lysosomal acid lipase substrate of the invention for a time sufficient to provide a solution comprising a lysosomal acid lipase enzyme product; and
(b) determining the quantity of the lysosomal acid lipase enzyme product.

In other embodiments, the invention provides methods for assaying lysosomal acid lipase, comprising:
(a) contacting a sample with a first solution to provide a first solution comprising lysosomal acid lipase;
(b) contacting the first solution comprising lysosomal acid lipase with a lysosomal acid lipase substrate of the invention and incubating the substrate with the enzyme for a time sufficient to provide a solution comprising a lysosomal acid lipase enzyme product; and
(c) determining the quantity of the lysosomal acid lipase enzyme product.

In the methods, the quantity of the lysosomal acid lipase enzyme product is determined by mass spectrometric analysis or fluorometric analysis.

In certain embodiments, the substrate is 4-propyl-7-palmitoyloxy-8-methylcoumarin.

In the methods, the sample is whole blood, serum, plasma, or a lysate obtained from a subject to be tested. Suitable lysates include cell lysates, such as leukocyte lysates, liver cell lysates, and fibroblast lysates. In certain embodiments, the sample is a dried blood spot (DBS) from the subject. In certain of these embodiments, the sample is a dried blood spot from newborn screening.

In a further aspect, the LAL assays of the invention can be used to provide information for diagnosing diseases and conditions attributable to LAL deficiency. For diagnosis, the mass spectrometric analysis or the fluorometer analysis further includes using the quantity of the lysosomal acid lipase enzyme product to determine whether the sample is from a candidate for treatment of a condition associated with lysosomal acid lipase deficiency, such as Wolman disease or cholesterol ester storage disease. In certain embodiments, the LAL assay is a newborn screening assay.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

Figure 3:
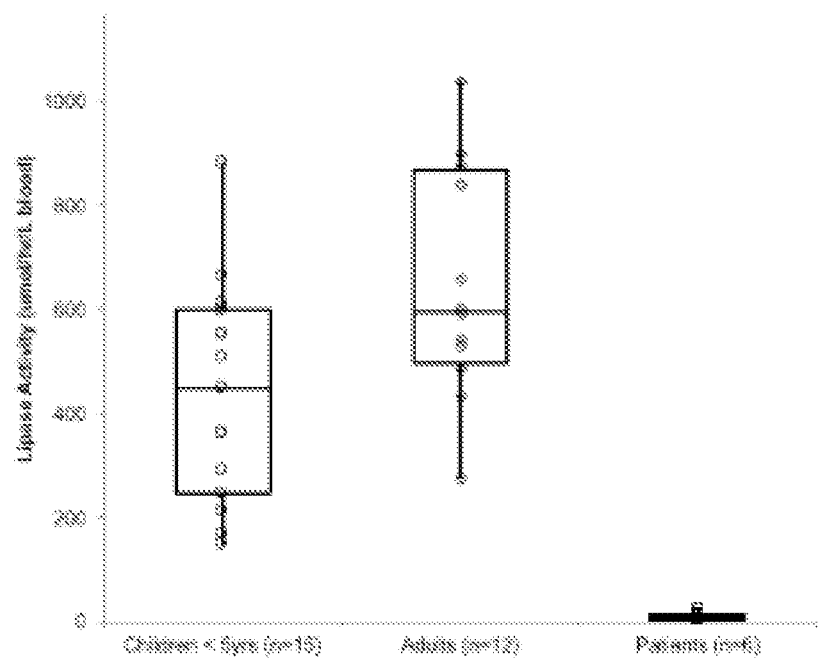

FIG. 3 shows LAL activity in DBS measured with substrate P-PMHC and ultra performance liquid chromatography (UPLC)-MS/MS. The bottom of each box is the value of the first quartile, the middle line is the medium value, and the top line is the third quartile. All values are blank corrected. Individual patient values are given in FIG. 6.

Figure 4:
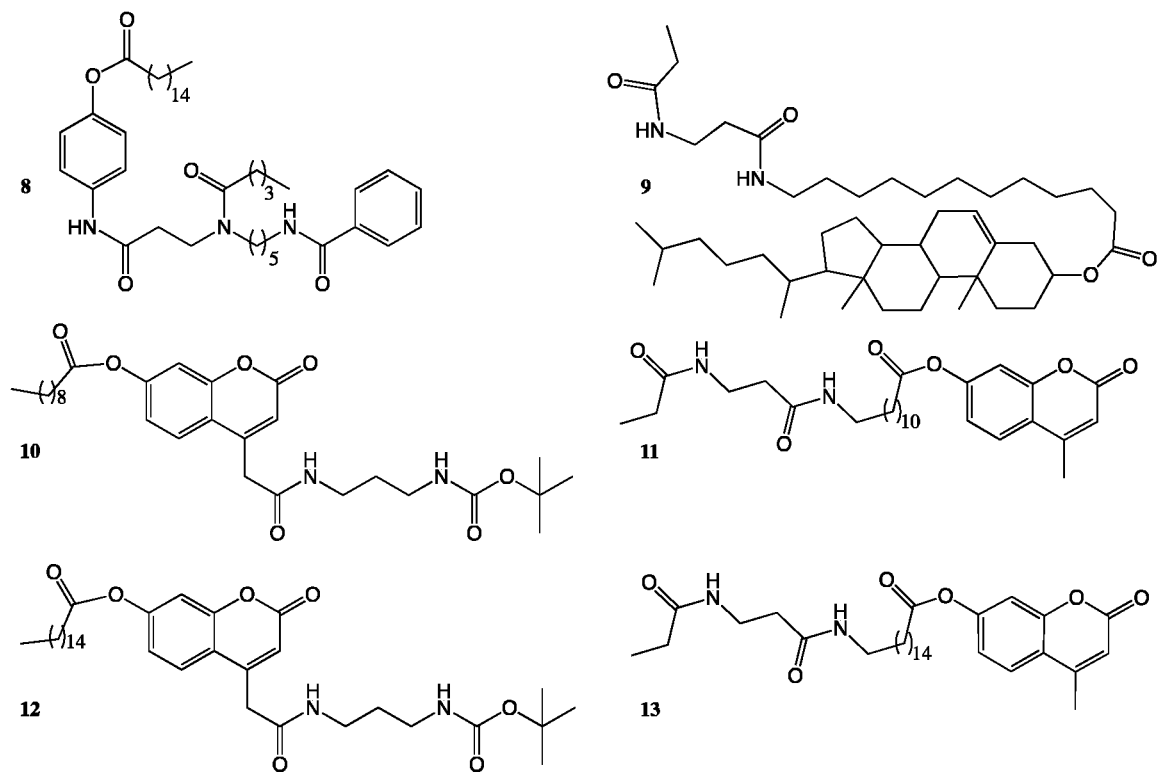

FIG. 4 shows the structure of compounds (Compounds 8-13) prepared for testing for specific LAL activity in DBS.

FIG. 5 shows the structures of coumarins (4MU) used to prepare the library of palmitoyl-4MU analogs (Compounds 1 and 14-37).

FIG. 6 is a summary of LAL activity for Compound 1 as LAL substrate as measured by UPLC-MS/MS.

DETAILED DESCRIPTION OF THE INVENTION

The present invention provides lysosomal acid lipase (LAL) substrates, assays for lysosomal acid lipase using the substrates, and methods for diagnosing diseases and conditions attributable to lysosomal acid lipase deficiency.

LAL Substrates

In one aspect, the invention provides LAL substrates. In certain embodiments, the LAL substrate is a compound having formula (I):

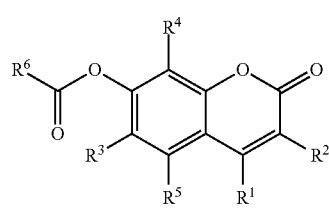

wherein
$R^1$ is selected from the group consisting of
(a) hydrogen,
(b) linear or branched C1-C6 alkyl (e.g., methyl, ethyl, n-propyl, n-butyl), optionally wherein one of the carbon atoms is replaced with an oxygen atom (i.e., to provide ethers, such as —CH$_2$OCH$_3$),
(c) linear or branched C1-C6 haloalkyl (e.g., CF$_3$),
(d) phenyl optionally substituted with one or more halo groups (e.g., 4-F phenyl) or a phenyl group,
(e) pyridyl (e.g., 4-pyridyl),
(f) C1-C3alkoxy C1-C3 alkyl (e.g., CH$_2$OCH$_3$), and
(g) N—C1-C3alkyl morpholino (e.g., NHCH$_2$N(CH$_2$CH$_2$)$_2$O);
$R^2$ is selected from the group consisting of
(a) hydrogen,
(b) linear or branched C1-C6 alkyl (e.g., methyl, ethyl), optionally wherein one of the carbon atoms is replaced with an oxygen atom,
(c) halo (e.g., Cl, Br),
(d) CN, and
(e) phenyl,
(f) halo-substituted phenyl (e.g., 2,4-Cl phenyl), and
(g) benzyl, or $R^1$ and $R^2$ taken together with the carbon atoms to which they are attached form a 5-, 6-, or 7-membered ring (e.g., —(CH$_2$)$_n$—, n=3-5);
$R^3$ is selected from the group consisting of
(a) hydrogen,
(b) linear or branched C1-C6 alkyl (e.g., methyl, ethyl), optionally wherein one of the carbon atoms is replaced with an oxygen atom,
(c) halo (e.g., Cl);
$R^4$ is selected from the group consisting of
(a) hydrogen, and
(b) linear or branched C1-C6 alkyl (e.g., methyl, ethyl), optionally wherein one of the carbon atoms is replaced with an oxygen atom;
$R^5$ is hydrogen; and
$R^6$ is a linear or branched C5-C17 alkyl or alkenyl group, optionally wherein one, two, or three of the carbon atoms are replaced with an oxygen atom (to provide one, two or three ether group(s)), wherein the alkenyl group includes one, two, three or four carbon-carbon double bonds, and wherein the alkyl or alkenyl group is optionally substituted with a phenyl group.

In certain of these embodiments, $R^1$ is hydrogen or linear C1-C6 alkyl (e.g., methyl, ethyl, n-propyl, n-butyl), $R^2$ is hydrogen or linear C1-C6 alkyl (e.g., methyl, ethyl), or $R^1$ and $R^2$ taken together with the carbon atoms to which they are attached form a 5-, 6-, or 7-membered ring (e.g., —(CH$_2$)$_n$—, n=3-5), $R^3$ is hydrogen or linear C1-C6 alkyl, $R^4$ is hydrogen or linear C1-C6 alkyl (e.g., methyl, ethyl), $R^5$ is hydrogen, and $R^6$ is —(CH$_2$)$_n$CH$_3$, wherein n is an integer from 5 to 17 (e.g., n=14).

In other embodiments, the invention provides LAL substrates having formula (II):

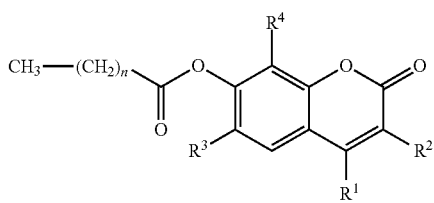

wherein
$R^1$ is selected from the group consisting of
(a) hydrogen,
(b) linear or branched C1-C6 alkyl (e.g., methyl, ethyl, n-propyl, n-butyl),
(c) linear or branched C1-C6 haloalkyl (e.g., CF$_3$),
(d) phenyl, and
(e) pyridyl (e.g., 4-pyridyl);
$R^2$ is selected from the group consisting of
(a) hydrogen,
(b) linear or branched C1-C6 alkyl (e.g., methyl, ethyl),
(c) benzyl,
(d) phenyl, and
(e) pyridyl (e.g., 4-pyridyl),
or $R^1$ and $R^2$ taken together with the carbon atoms to which they are attached form a 5-, 6-, or 7-membered ring (e.g., —(CH$_2$)$_n$—, n=4);
$R^3$ is selected from the group consisting of
(a) hydrogen,
(b) linear or branched C1-C6 alkyl (e.g., methyl, ethyl),
(c) halo (e.g., Cl);

$R^4$ is hydrogen or linear or branched C1-C6 alkyl (e.g., methyl); and n is an integer from 4 to 16.

In certain embodiments, the compounds of formula (II) are as follows:

$R^1$ is propyl (e.g., n-propyl), $R^2$ and $R^3$ are hydrogen, and $R^4$ is methyl (Compound 1);

$R^1$ is phenyl and $R^2$, $R^3$, and $R^4$ are hydrogen (Compound 15);

$R^1$ is trifluoromethyl, $R^2$ is hydrogen, $R^3$ is chloro, and $R^4$ is hydrogen (Compound 19);

$R^1$ is butyl (e.g., n-butyl) and $R^2$, $R^3$, and $R^4$ are hydrogen (Compound 20);

$R^1$ is methyl, $R^2$ is hydrogen, $R^3$ is chloro, and $R^4$ is hydrogen (Compound 22);

$R^1$ and $R^2$ taken together with the carbons to which they are attached form a 6-membered ring (e.g., —$(CH_2)_n$—, n=4), $R^3$ is ethyl, and $R^4$ is hydrogen (Compound 26);

$R^1$ is methyl, $R^2$ is ethyl, and $R^3$ and $R^4$ are hydrogen (Compound 27);

$R^1$, $R^3$, and $R^4$ are hydrogen and $R^2$ is phenyl (Compound 31);

$R^1$ is ethyl, $R^2$ and $R^3$ are hydrogen, and $R^4$ is methyl (Compound 32); and $R^1$ is pyridyl (e.g., 4-pyridyl) and $R^2$, $R^3$, and $R^4$ are hydrogen (Compound 33).

In certain of these embodiments, n is 14 (e.g., palmitolyl esters).

In one embodiment, the LAL substrate is the palmitoyl ester of 4-propyl-8-methyl-7-hydroxycoumarin(4-propyl-8-methyl-7-palmitoyloxycoumarin) (P-PMHC) (Compound 1).

In another embodiment, the LAL substrate is the palmitoyl ester of 3-ethyl-4-methyl-7-hydroxycoumarin(3-ethyl-4-methyl-7-palmitoyloxycoumarin) (Compound 27).

In a further embodiment, the LAL substrate is a compound of formula (II) wherein $R^1$ and $R^2$ taken together with the carbon atoms to which they are attached form a 6-membered ring, $R^3$ is ethyl, $R^4$ is hydrogen, and n is 14 (Compound 26).

In certain embodiments, the compounds of formula (II) have $R^1$, $R^2$, $R^3$, and/or $R^4$ as described above for formula (I).

LAL Assays

In another aspect of the invention, LAL assays are provided.

In certain embodiments, the invention provides methods for assaying lysosomal acid lipase, comprising:

(a) incubating a sample with a lysosomal acid lipase substrate of the invention for a time sufficient to provide a solution comprising a lysosomal acid lipase enzyme product; and (b) determining the quantity of the lysosomal acid lipase enzyme product.

In other embodiments, the invention provides methods for assaying lysosomal acid lipase, comprising:

(a) contacting a sample with a first solution to provide a first solution comprising lysosomal acid lipase;

(b) contacting the first solution comprising lysosomal acid lipase with a lysosomal acid lipase substrate of the invention and incubating the substrate with the enzyme for a time sufficient to provide a solution comprising a lysosomal acid lipase enzyme product; and (c) determining the quantity of the lysosomal acid lipase enzyme product.

In the methods, the quantity of the lysosomal acid lipase enzyme product is determined by mass spectrometric analysis or fluorometric analysis.

The methods of the invention include a single incubation step and do not include the use of Lalistat-2.

In certain embodiments, the substrate is 4-propyl-7-palmitoyloxy-8-methylcoumarin.

In the methods, the sample is whole blood, serum, plasma, or a lysate. Suitable lysates include cell lysates, such as leukocyte lysates, liver cell lysates, and fibroblast lysates. In certain embodiments, the sample is a dried blood spot (DBS) from a subject. In certain of these embodiments, the sample is a dried blood spot from newborn screening.

In certain embodiments, the sample is first treated with a first solution, such as water.

In certain embodiments, incubating the substrate with the enzyme for a time sufficient to provide a solution comprising a lysosomal acid lipase enzyme product comprises incubating at 37° C. for 3 hours. Suitable incubation temperatures range from 15-50° C. and incubation times from 30 min to 2 days.

In certain embodiments, the methods further include contacting the first solution comprising lysosomal acid lipase with a phospholipid (e.g., cardiolipin) prior to incubation.

In certain embodiments, the methods further include contacting the sample or first solution comprising lysosomal acid lipase with an internal standard prior to incubation. Suitable internal standards include isotopically labeled lysosomal acid lipase enzyme products. Representative internal standards include carbon-13-labeled 4-propyl-8-methyl-7-hydroxycoumarin (see internal standard 3 in FIG. 1).

In certain embodiments, the methods further include quenching the incubation prior to determining the quantity of the lysosomal acid lipase enzyme product.

As noted above, in certain embodiments, the quantity of the lysosomal acid lipase enzyme product is determined by mass spectrometric analysis (e.g., tandem mass spectrometry (MS/MS)). In certain of these embodiments, quenching comprises the adding water and an organic solvent (e.g., ethyl acetate) to the solution comprising the lysosomal acid lipase enzyme product. In these embodiments, the solution comprising a lysosomal acid lipase enzyme product is extracted with an organic solvent to provide a solution of the lysosomal acid lipase enzyme product in the organic solvent. The organic solvent is then removed to provide isolated lysosomal acid lipase enzyme product. The isolated lysosomal acid lipase enzyme product is then dissolved in an aqueous solvent (e.g., aqueous methanol, such as water/methanol 1:1) and conducted to a mass spectrometer by liquid chromatography or by flow injection.

In other embodiments, the quantity of the lysosomal acid lipase enzyme product is determined by fluorometric analysis. In certain of these embodiments, quenching comprises adding an aqueous solvent (e.g., aqueous methanol, such as water/methanol 1:1) to the solution comprising the lysosomal acid lipase enzyme product. In certain embodiments, the fluorometric analysis is performed with an excitation wavelength of 355 nm and an emission wavelength at 460 nm.

Diagnostic Methods

The LAL assays of the invention can be used to provide information for diagnosing diseases and conditions attributable to LAL deficiency. For diagnosis, the mass spectrometric analysis or the fluorometer analysis further includes using the quantity of the lysosomal acid lipase enzyme product to determine whether the sample is from a candidate for treatment of a condition associated with lysosomal acid lipase deficiency, such as Wolman disease or cholesterol ester storage disease. In certain embodiments, the LAL assay is a newborn screening assay. For certain of these assays, the quantity of the lysosomal acid lipase enzyme product is determined by mass spectrometric analysis and the method is multiplexed with other newborn screening lysosomal storage disease assays (e.g., MS/MS methods).

The following is a description of representative LAL substrates and LAL assays of the invention.

Development of the LAL Assay

The present invention provides a LAL assay that utilizes a substrate that is acted upon only by LAL in DBS, thus avoiding the need to carry out two assays in parallel in the presence and absence of the LAL-specific inactivator Lalistat-2 (as described in Hamilton et al., *Clin Chim Acta* 2012; 413:1207-10). Choices for LAL substrate include natural LAL substrates, cholesterol esters, and triglycerides. By carrying out the assay described by Hamilton et al. with palmitoyl-4MU on a DBS extract and also with known amounts of recombinant LAL, it was determined that there was no more than 50 to 100 pg of LAL in the DBS extract. Using this value and the published specific activities for purified LAL acting on the natural substrates cholesterol oleate and triolein (*Anal Biochem* 1985; 145:398-405), it was concluded that the amount of products produced with a 3-mm DB punch and the natural substrates would be well below the detection limits for mass spectrometry. Thus, the assays using these natural substrates would be insufficient.

A variety of new fatty acid esters as possible substrates for LAL were evaluated. Variants of palmitoyl-4MU containing replacements for the 4MU group were tested (Compound 1). Also tested was the ester formed between cholesterol and a fatty acyl group containing a bis-amide at the ω end of the acyl chain (Compound 2). Analogs of palmitoyl-4MU containing alkyl-amide chains attached to the methyl of the 4MU moiety (Anal Chem 2011;83:1152-6) were also tested (Compounds 3 and 5). Finally, analogs of palmitoyl-4MU containing bis-amides at the ω terminus of the fatty acyl group of palmitoyl-4MU (Compound 4 and 6) were tested. None of these compounds displayed detectable LAL activity when tested with DBS. These studies show that addition of polar groups to the palmitoyl chain abrogated activity toward LAL. Also, extension of the 4MU moiety with polar chains was also not tolerated.

The only substrate that displayed measurable LAL activity using DBS was palmitoyl-4MU. This is presumably because of the highly reactive nature of the ester linkage to the strong leaving group 4MU and the fact that LAL prefers highly hydrophobic substrates.

A library of compounds that contained relatively small structural variations of the palmitoyl-4MU substrate was prepared. The structures of all library components are shown in FIG. 5. From this library of twenty-five (25) compounds, P-PMHC (FIG. 1) emerged as the substrate with the best combination of high specific activity on LAL and high specificity for LAL. Therefore, additional studies utilized with P-PMHC.

A variety of phospholipids were evaluated as replacements for cardiolipin, which was used in the original LAL assay described by Hamilton et al. (*Clin Chim Acta* 2012; 413:1207-10). The following phospholipids were tested individually at 0.1 mmol/L: 1,2-dioleoyl-phosphatidylethanolamine, 1,2-dioleoyl-phosphatidylmethanol, 1,2-dioleoyl-phosphatidylcholine, 1,2-dioleoyl-phosphatidylserine, brain phosphatidylethanolamine, 1,2-heptadecyl-phosphatidylcholine, and 1,2-lauryl-phosphatidylcholine. None of these phospholipids led to any substantial increase in LAL over that measured with cardiolipin; thus, studies were continued with the latter.

In the original assay described by Hamilton et al. (*Clin Chim Acta* 2012; 413:1207-10), DMSO was used as a solvent to prepare the palmitoyl-4MU and Lalistat-2 stock solutions. The final concentration of DMSO in the LAL assay was 2.4%. Over the course of the studies, it was noticed that the quality of the DMSO was critical to being able to detect LAL activity in DBS. Previously opened bottles of DMSO stored for approximately 1 month or longer led to essentially complete loss of LAL activity measured in DBS. Based on this result, DMSO was replaced with dimethylformamide for preparation of the substrate stock solution, and to use ethanol to prepare the Lalistat-2 solution (however, with the use of LAL-specific P-PMHC, Lalistat-2 was no longer used). In the final assay conditions, ethanol was used as the only solvent other than water.

The original LAL assay described by Hamilton et al. (*Clin Chim Acta* 2012; 413:1207-10) used Triton X-100 as the detergent, which was replaced this with sodium taurodeoxycholate because this detergent largely remains in the aqueous phase following liquid-liquid extraction with ethyl acetate (thus minimizing injection of large amounts of detergent onto the UPLC column). Replacement of Triton X-100 with 2.5 mmol/L sodium taurodeoxycholate resulted in a 20% decrease of LAL activity, and increasing the detergent concentration further led to an additional loss of activity. Thus, 2.5 mmol/L was chosen for all subsequent studies.

Figure 2:
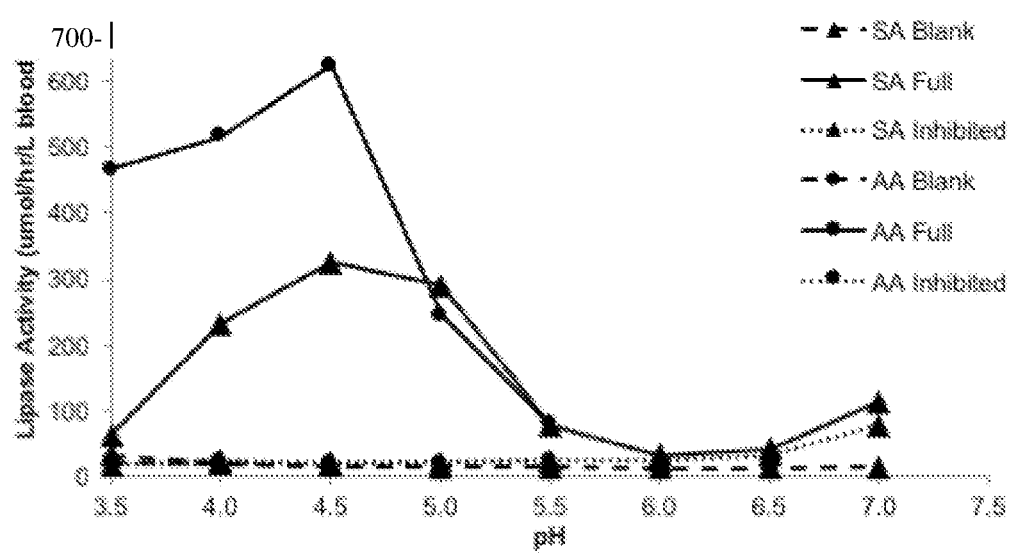
FIG. 2 shows pH rate profile for recombinant human LAL activity using substrate P-PMHC from pH 3.5 to 7.0: complete assay in 0.1 mol/L succinate (filled circles); complete assay in 0.1 mol/L sodium acetate (open circles); no enzyme blank in 0.1 mol/L succinate (filled triangles); complete assay in 0.1 mol/L succinate with Lalistat-2 inhibition (open squares). Buffer (9 volumes) was combined with 2.5 mmol/L sodium taurodeoxycholate, 3.7 mmol/L substrate P-PMHC, and 1 volume of 0.5% (w/v) cardiolipin in ethanol. Full assays were carried out with DBS extract from a healthy adult and in the absence of Lalistat-2. Blank assays were carried out using water and 300 μmol/L Lalistat-2. Inhibited assays were carried out as for the full assays but in the presence of 300 μmol/L Lalistat-2.

The LAL pH rate profile was studied from 3.5 to 7.0 in 0.1 mol/L succinate or from 3.5 to 5.5 in 0.1 mol/L sodium acetate (FIG. 2). Based on this, 0.1 mol/L sodium acetate, pH 4.5 was used to maximize LAL activity.

A concentration of P-PMHC in the mixture of 3 mmol/L was settled on based on a combination of high LAL activity and minimal background. The original assay described by Hamilton et al. (*Clin Chim Acta* 2012; 413:1207-10) used 40 µL of an aqueous extract of a 3-mm DBS added to 160 µL of assay mixture. To keep the solvent volumes for the liquid-liquid extraction to a minimum, thus avoiding long times for solvent removal, 10 µL of an aqueous extract of a 3-mm DBS punch was added to 30 µL of assay mixture.

Figure 1:
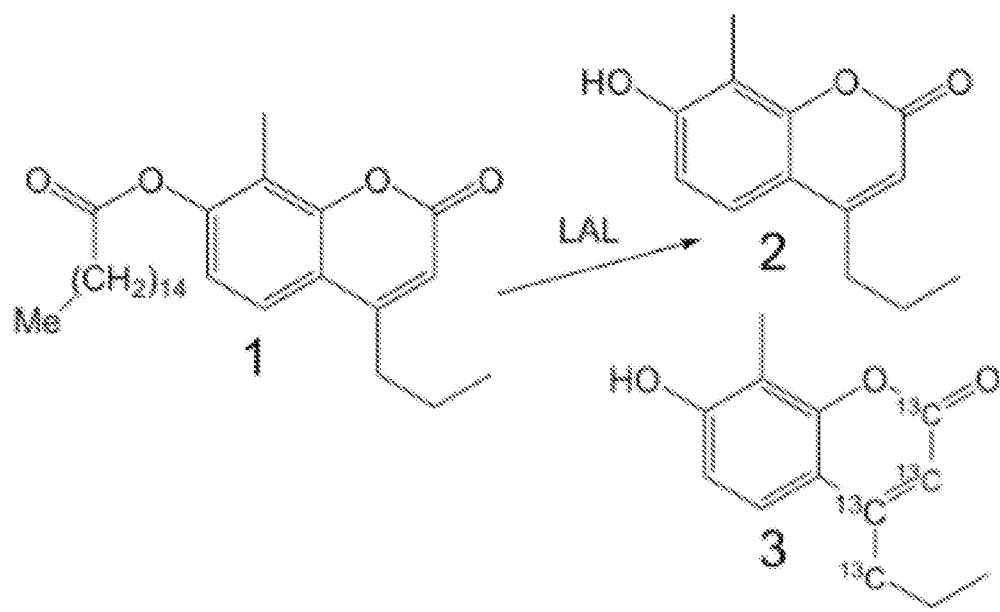
FIG. 1 shows the structure of LAL-specific substrate P-PMHC (palmitoyl ester of 4-propyl-8-methyl-7-hydroxycoumarin) (4-propyl-7-palmitoyloxy-8-methylcoumarin), the corresponding LAL product, and the heavy atom substituted internal standard.

With the final assay conditions chosen, a specific activity of 874 µmol/h/L was obtained using a 3-mm punch of a DBS from a healthy adult. The activity was measured by UPLC-MS/MS after extraction of the reaction mixture with ethyl acetate. The tandem mass spectrometry multiple reaction monitoring response was converted to micromoles of product with the use of a chemically identical but isotopically differentiated internal standard (carbon 13-labeled 4-propyl-8-methyl-7-hydroxycoumarin) (FIG. 1). The use of the internal standard accounts for all product losses owing to sample processing and analysis. Using a 3-mm punch from an identical DBS and the previous fluorometric LAL assay with and without Lalistat-2, a specific activity of 466 µmol/h/L (within the range of values reported previously) for the LAL component was obtained, which is 1.9-fold lower than the activity measured with the UPLC-MS/MS assay described herein.

The following studies established that LAL substrate P-PMHC was highly specific for LAL in DBS (Table 1). When extracts from two healthy persons' DBS were preincubated with 10 µmol/L Lalistat-2, 98% of the activity toward P-PMHC was inhibited. This increases to 99% inhibition if 100 µmol/L Lalistat-2 was used (Table 1). In contrast, when the same DBS extract was submitted to the previously reported assay with palmitoyl-4MU (Hamilton et al., *Clin Chim Acta* 2012; 413:1207-10), 78% of the total lipase activity was blocked by 10 μmol/L Lalistat-2. Under the assumption that Lalistat-2 was completely selective for LAL, the data showed that P-PMHC, but not palmitoyl-4MU, was highly specific for LAL in DBS.

TABLE 1

Effect of Lalistat-2 on the activity (tandem mass spectrometry method) of LAL toward substrate P-PMHC.[a]

| DBS | Activity without Lalistat-2, μmol/h/L | Activity with 10 μmol/L Lalistat-2, μmol/b/L | Activity with 100 μmol/L Lalistat-2, μmol/h/L |
|---|---|---|---|
| Adult 1 (triplicate) | 554, 582, 582 | 10, 9, 10 | 6, 4, 5 |
| Adult 2 (triplicate) | 519, 539, 473 | 5, 2, 3 | 2, 0, 1 |
| Blank (15 measurements) | | 16.8-26.2 | |

[a]Activity values for the adult DBS were blank corrected. Tire blank was obtained by using an equal volume of water instead of water-extracted DBS.

Fluorometric LAL Assay

Because hydrolysis of P-PMHC leads to the fluorescent product 4-propyl-8-methyl-7-hydroxycoumarin, a standard plate reader fluorometer was used to measure LAL activity in DBS. Table 2 shows LAL activities measured with UPLC-MS/MS and by fluorometry on an identical set of DBS from 10 adults.

Patient Samples

FIG. 3 shows the LAL activity data in DBS from fifteen (15) healthy children (<5 years old), twelve (12) healthy adults, and six (6) patients previously shown to be LAL-deficient. All patients had symptoms consistent with LAL deficiency, and these six (6) patients were shown to be LAL-deficient by the original LAL assay method on DBS (Hamilton et al., *Clin Chim Acta* 2012; 413:1207-10). The patients are deidentified, and there was no additional information.

All assays were carried out with UPLC-MS/MS using the optimized conditions with substrate P-PMHC in the absence of Lalistat-2 (thus, only a single assay per patient was needed). Individual values are shown in FIG. 6. All healthy persons showed LAL activity well separated from that measured with LAL-deficient patients. The fact that LAL activity was close to zero in all six (6) LAL-deficient patients was further evidence that substrate P-PMHC was LAL-specific.

The LAL assay of the invention described herein makes use of a substrate that is highly specific for LAL, thus allowing its activity to be measured in DBS using a single incubation. In contrast, about one third of the standard substrate used to assay LAL, palmitoyl-4MU, is hydrolyzed by ≥1 esterases/lipases in DBS other than LAL. In the original assay, the LAL activity is obtained as the fraction of

TABLE 2

LAL activity in DBS measured by UPLC-MS/MS and fluorometric assays.

| Type | Samples | LAL activity, μmol/h/L blood[a] | Mean | % CV |
|---|---|---|---|---|
| Fluorescence | 1 | 746, 707, 596, 599 | 662 | 9.94 |
| Adult | 2 | 541, 751, 675, 519, 803 | 658 | 17.08 |
| | 3 | 618, 592, 583, 628 | 605 | 3.05 |
| | 4 | 933, 1683, 1073, 938, 1261, 1348 | 1206 | 21.81 |
| | 5 | 809, 917, 901, 768, 815 | 842 | 6.83 |
| | 6 | 1198, 1635 1361, 1382, 1284 | 1372 | 10.67 |
| | 7 | 758, 854, 841, 645, 781 | 794 | 9.95 |
| | 9 | 427, 100, 376, 239 | 286 | 44.54 |
| | 10 | 767, 857, 1150, 1158, 900 | 980 | 15.89 |
| | 12 | 989, 843, 792, 918, 604, 703 | 808 | 15.89 |
| Blank[b] | | 48-78 | 58 | 19.03 |
| UPLC-MS/MS | 1 | 598, 555, 653, 578, 608 | 598.5 | 5.5 |
| Adults | 2 | 712, 701, 674, 632, 588, 636 | 657.1 | 6.5 |
| | 3 | 492, 499, 506, 480, 453, 465 | 482.2 | 3.9 |
| | 4 | 962, 842, 862, 848, 1016, 849 | 896.3 | 7.5 |
| | 5 | 846, 852, 852, 864, 923, 907 | 874.0 | 3.4 |
| | 6 | 990, 979, 1129, 1152, 929 | 1035.8 | 8.5 |
| | 7 | 613, 555, 488, 536, 514, 470 | 529.0 | 8.9 |
| | 9 | 316, 330, 220, 247, 292, 236 | 273.4 | 15.2 |
| | 10 | 938, 796, 818, 627, 1112, 740 | 838.3 | 18.3 |
| | 12 | 424, 534, 376, 496, 368, 385 | 430.4 | 14.7 |
| Blank[b] | | 6.3-24.9 | 15 | 36.4 |

[a]Activity values are blank corrected.
[b]Range of blank values given for 12 and 56 repeats of the fluorometric and tandem mass spectrometry assays, respectively.

Agreement between the two assays generally showed <30% difference in activity values for all but 1 pair, for which the difference approached 50%.

The analytical range is an important assay parameter that is defined as the ratio of assay response measured with the quality control high sample (typical of a healthy person) divided by the assay response for all elements independent of LAL (*Clin Chem* 2015; 61:1363-71). The larger the analytical range, the greater the activity values will be spread out, leading to greater accuracy especially when activity is low. The mean analytical range for the UPLC-MS/MS assay was forty-four (44) compared with a value of fourteen (14) for the fluorometric assay.

palmitoyl-4MU hydrolase activity that is sensitive to Lalistat-2 (Hamilton et al., Clin Chim Acta 2012; 413:1207-10). Because the LAL activity component is obtained as the difference in two substantial activity values, the error in LAL activity must include the propagation of errors in two separate measurements. Thus, it would be required to raise the cutoff value in a newborn screening program based on the Lalistat-2 method. This would result in an increase in the false-positive rate. With the LAL-specific substrate P-PMHC described herein, not only can the effort to perform the assay be reduced, but the screen cutoff can also be lowered.

It has been shown by comparison of large pilot newborn screening studies of lysosomal storage diseases that the tandem mass spectrometry enzymatic activity method gives a substantially lower number of positive screenings than the fluorometric method when compared at equivalent cutoff values (Mol Genet Metab 2016; 118:304-9). This may be because the analytical range of the tandem mass spectrometry assays is >3-fold greater than that of the corresponding fluorometric assays (*Clin Chem* 2015; 61:1363-71). Thus, the use of UPLC-MS/MS may be the method of choice for newborn screening of LAL deficiency.

The UPLC-MS/MS LAL assay described herein may be multiplexed with other tandem mass spectrometry assays for lysosomal storage diseases simply by addition of substrate P-PMHC to a single assay mixture containing a collection of additional substrates and internal standards and performing a single UPLC-MS/MS in which all products and internal standards are detected by multiple reaction monitoring mode.

Materials and Methods

All patient samples were obtained with Institutional Review Board approval from the University of Washington. DBS from anonymized samples from LAL-deficient patients were obtained from Dr. Rhona Jack (Seattle Children's Hospital). All patient samples were stored at 4° C. in sealed plastic bags. Other DBS samples were stored in plastic bags at −20° C. in sealed containers with desiccant.

Recombinant LAL was obtained as a gift from Alexion Corp. The synthesis of reagents is detailed below. Lalistat-2 was provided as a gift from Dr. J. Hamilton (Yorkhill Hospital, UK) or synthesized as described (*J Med Chem* 2007; 50:5449-56).

LC-MS/MS LAL Assay

Assay mixture was prepared by combining 9 volumes of 0.1 mol/L sodium acetate buffer (made by adding reagent grade NaOH to 0.1 mol/L reagent-grade acetic acid in water), pH 4.5, containing 2.5 mmol/L sodium taurodeoxycholate hydrate (Sigma, 287245) with 1 volume of 0.5% (w/v) bovine heart cardiolipin in ethanol (Sigma, C1649) containing 3 mmol/L substrate palmitoyl 4-propyl-8-methyl-7-hydroxycoumarin (P-PMHC) and 50 µmol/L carbon-13-labeled 4-propyl-8-methyl-7-hydroxycoumarin (internal standard). The latter was prepared by mixing solid substrate P-PMHC with internal standard solution in absolute ethanol, removing solvent in a centrifugal concentrator under vacuum (or with a jet of nitrogen), and then mixing with commercial cardiolipin/ethanol solution. This ethanol stock could be stored at −20° C. for several months (avoid>2-3 freeze-thaw cycles), and the aqueous buffer could be stored at 4° C. for several months. This was based on no change in assay results when new and stored solutions were used. Assay mixture was made fresh before each use.

To a 3-mm punch from a DBS in a 1.5-mL polypropylene Eppendorf tube was added 200 µL of purified water (Milli-Q, EMD Millipore). The tubes were shaken on an orbital platform shaker for 1 h at ambient temperature. The tube of DBS extract was mixed briefly on a vortex-type mixer, and a 10 µL aliquot was added to the well of a polypropylene, deep-well, 96-well plate (Costar, 3959). Assay mixture (30 µL, ambient temperature) was added to each well. The plate was centrifuged at 3000 g for 5 min at ambient temperature to ensure that all liquid was at the well bottom. The plate was sealed with a film cover (Advantage 96-well round clear Silicone/PTFE cap mat 962611). The plate was shaken at 37° C. in an incubator with orbital mixing at 400 rpm for 3 h. The reactions were quenched by addition of 80 µL of purified water (Milli-Q, EMD Millipore) followed by 400 µL of HPLC-grade ethyl acetate. The well contents were mixed by pipetting up and down approximately 10 times. The plate was centrifuged at 3000 g for 5 min at ambient temperature, and then 120 µL of the upper ethyl acetate layer was transferred to a shallow-well, 96-well polypropylene plate (Greigner, 651201). Solvent was removed at ambient temperature with a jet of nitrogen. To each well was added 200 µL of water/methanol (1:1, Fisher Optima Grade), and samples were mixed by pipetting up and down a few times. The plate was wrapped with aluminum foil and placed in the autosampler chamber at 8° C. in preparation for LC-MS/MS analysis.

Liquid chromatography was carried out using a Waters Acquity binary solvent pump system with a CSH, C18, 1.7-µm, 2.1×50-mm column (Waters, 186005296) and a CSH, C18, 1.7-µm guard column (Vanguard, 186005303). The solvent program was 99% A (70:30, water/acetonitrile, 0.1% formic acid, Fisher Optima grade)/1% B (50:50, acetonitrile/isopropanol, 0.1% formic acid) to 30% A/70% B over 1 min, then jump to 100% B and hold for 0.5 min, then to 99% A over 0.5 min (flow rate 0.8 mL/min). The total run time was 2.5 min. Mass spectrometry was carried out with a Waters Xevo TQ tandem-quadrupole instrument. Additional liquid chromatography and tandem mass spectrometry parameters are provided in Table 3.

Fluorometric LAL Assay

The fluorometric assay up to the end of the incubation was identical to the LC-MS/MS assay, except no internal standard was present in the stock substrate solution. After incubation, the fluorometric assay was continued as follows:

Reactions were quenched by addition of 200 µL of water/methanol (1:1, Fisher Optima Grade). The well contents were mixed by pipetting up and down approximately 10 times. A portion (150 µL) of the well contents was transferred to a black, flat-bottomed 96-well microtiter plate (NUNC 437112). Samples were immediately read on a fluorometer (PerkinElmer Victor3V 1420) with an excitation wavelength of 355 nm, an emission wavelength of 460 nm, and an excitation time of 0.1 s. The fluorometer reading was converted to micromoles of product by generating a standard curve. DBS extract (60 µL) and assay mixture (450 µL) were incubated separately. To a well was added 200 µL of water/methanol solution (1:1), 10 µL of DBS extract, and 30 µL of assay mixture. To each well was added 2 µL of LAL product (4-propyl-8-methyl-7-hydroxycoumarin) (0, 0.2, 1, or 2 nmol) from an aqueous stock solution. After mixing by pipetting up and down approximately 10 times, a 150 µL aliquot was transferred to the fluorometer plate and submitted to fluorometry as above. The well in which no product 2 was added serves as the blank. Note that because DBS extract and assay mixture were incubated separately, this blank reflected (a) the fluorescence of the blood extract and substrate; (b) any fluorescence owing to nonenzymatic breakdown of substrate; and (c) any quenching of the fluorescence by components of the blood.

Fatty Acid Ester Synthesis, Characterization, and Substrate Activity

The synthesis, characterization, and activity as LAL substrate of substituted coumarin fatty acid esters are described below.

Fatty Acid Esters

The general synthesis of fatty acid esters involving substituted coumarins is described here using the following as an example.

7-Hydroxy-8-methyl-4-propyl-2H-chromen-2-one (8 mg, 0.04 mmole, Chembridge 6367113) and potassium tert-butoxide (0.04 mmole) were placed in an oven-dried flask under argon. Dry tetrahydrofuran (2 mL) was added, and the mixture was stirred for 10 min at ambient temperature. Palmitoyl chloride (0.03 mmole) was added via a Hamilton glass syringe, and the mixture was stirred overnight at ambient temperature under argon. The reaction was quenched by addition of water, and the solution was extracted with methylene chloride. The organic extract was dried over anhydrous sodium sulfate, filtered and concentrated. Product was purified by reverse phase HPLC on a C18 column (YMC-Pack ODS-A, 100×20 mm, 5 mm, Waters, AA12S05-1020WT) with the following solvent gradient: 80% water/20% acetonitrile for 5 min, then to 100% acetonitrile over 35 min, then hold at 100% acetonitrile for 10 min. The product eluted at approximately 45 min. Solvent was removed with a vacuum centrifuge at ambient temperature. The structure of the product was confirmed by $^1$H-NMR and electrospray ionization mass spectrometry.

Assay Internal Standard 3

To a flame-dried flask was added solid sodium hydride (3.8 mmole) and 12 mL of dry tetrahydrofuran at 0° C. under nitrogen. The mixture was stirred for 15 min. Then ethyl acetoacetate-1,2,3,4-13C4 (0.3 mL, 2.5 mmole, Sigma Cat. 489263) was added dropwise. Stirring was continued for 15 min. n-Butyl lithium (1.6 M in hexane, 3.8 mmole) was added dropwise via syringe, and stirring was continued at 0° C. Ethyl bromide (4 mmole) was added dropwise, then the reaction was allowed to warm to room temperature with stirring for 30 min. The reaction was quenched with water then extracted with ethyl acetate. The organic layer was washed with brine then dried over anhydrous sodium sulfate. After filtration and solvent removal, the crude product was purified using a silica column with hexane/ethyl acetate. Ethyl 3-oxohexanoate (0.3 mmole) was mixed with 2-methyl-resorcinol (0.3 mmole) and 2 drops of concentrated sulfuric acid. The mixture was heated in a sealed tube in a microwave reactor (10 min, 100° C., 400 Watts). The reaction was quenched with water and extracted with dichloromethane. After drying the organic layer with anhydrous sodium sulfate, filtration, and solvent removal, the crude product was purified by HPLC (same column and gradient as above). The coumarin eluted at ~70% B.

A stock solution of internal standard was prepared by weighing>5 mg of labeled coumarin and adding absolute ethanol (stored at −20° C.) in a Teflon-septum, screw cap vial.

UPLC-MS/MS Parameters

UPLC was carried out as described below. Ten mL of sample was injected in full-loop mode. The weak needle wash was water/acetonitrile (90/10) with 0.1% formic acid, and the strong needle wash was 100% acetonitrile with 0.1% formic acid.

TABLE 3

MS/MS Parameters and settings.

| Parameter | Value |
| --- | --- |
| Capillary Voltage | 2.95 kV |
| Extractor Voltage | 3 V |

TABLE 3-continued

MS/MS Parameters and settings.

| Parameter | Value |
| --- | --- |
| Desolvation Temperature | 450° C. |
| Source Temperature | 150° C. |
| Desolvation Gas Flow | 850 L/hr |
| Cone Gas Flow | 30 L/hr |
| Collision Gas Flow | 0.15 mL/min |
| LM Resolution 1 | 2.82 |
| HM Resolution 1 | 14.92 |
| Ion Energy 1 | 0.8 |
| LM Resolution 2 | 2.88 |
| HM Resolution 2 | 14.7 |
| Ion Energy 2 | 1.1 |
| Aperture | 0.1 |
| Entrance | 0.5 |
| Exit | 0.5 |
| Gain | 1 |

TABLE 4

Multiple Reaction Monitoring Parameters.[1]

| Compound | Parent (m/z) | Daughter (m/z) | Dwell (s) | Cone (V) | Collision (V) |
| --- | --- | --- | --- | --- | --- |
| Product 2 | 219.1 | 190 | 0.05 | 40 | 22 |
| Internal Standard 3 | 223.1 | 194 | 0.05 | 40 | 22 |

[1]All data for activity of Substrate 1 was determined from the ratio of the traces of Product 2 over Internal Standard 3.

Testing Potential LAL Substrates with Recombinant LAL and DBS

FIG. 4 shows the structures of six potential LAL substrates (Compounds 8-13) that were synthesized and tested for LAL specific activity in DBS samples. Compound 8 was a palmitoylated ester. Compound 9 was a cholesterol ester synthesized to have a terminal bis-amide. Compounds 10 and 12 were two different chain-length variants of an existing coumarin-like scaffold. Compounds 11 and 13 were two chain-length 4-methylumbelliferone ester variants with terminal bis-amides.

These compounds were tested for LAL activity as follows:

Compound 8. Assay cocktail contained 0.69 mM Compound 8, 10 mM internal standard (analog of the product containing an n-hexanoyl amide tail instead of the n-pentanoyl amide tail) in 0.15 M sodium acetate, pH 4.02, containing 0.1% Triton X-100. Assay cocktail (30 mL) was added to a 3 mm DBS punch from a normal adult and 10 mL of 30 mM aqueous Lalistat-2 or H$_2$O was added, and the mixture was incubated at 37° C. for 16 hr in an Eppendorf tube with orbital shaking at 250 rpm. The assay was quenched by addition of 120 mL of acetonitrile. The sample was centrifuged for 5 min at 3000×g, and 120 mL of supernatant was transferred to an autosampler plate. Water (60 mL) was added to the well, and 10 mL was injected for UPLC-MS/MS. Compound 8 product was analyzed by UPLC-MS/MS using the authentic product as a standard to establish UPLC and MS/MS conditions.

Compound 9. Assay cocktail contained 0.3 mM Compound 9 (from a 10 mM DMSO stock) in a 14:1 solution of 0.15 M sodium acetate pH 4.0 1% Triton-X-100 and 0.5% m/v cardiolipin in methanol. For DBS tests, 20 mL of rehydrated blood mixture (from a 3 mm DBS punch resuspended in 200 mL of H$_2$O for 1 hr at RT with orbital shaking) was added to 75 mL of assay cocktail and incubated at 3TC for 12 hrs in an Eppendorf tube with orbital shaking at 250 rpm. For recombinant LAL tests, 1 mL of diluted enzyme solution (prepared from a 2 mg/mL stock diluted serially by 10-fold twice in H$_2$O) was added to 19 mL of H$_2$O. The process was then the same as for the DBS version. The assay was quenched by addition of 120 mL of acetonitrile. The sample was centrifuged for 5 min at 3000× g, and 120 mL of supernatant was transferred to an autosampler plate. Water (120 mL) was added to the well, and 10 mL was injected for UPLC-MS/MS. Compound 9 product was analyzed by UPLC-MS/MS using the authentic product as a standard to establish UPLC and MS/MS conditions.

Compounds 10-13. Assay cocktail contained 0.345 mM 10-13 (from a 13.3 mM DMSO or DMF stock) in a 14:1:0.4 solution of 0.15 M sodium acetate pH 4.0 1% Triton-X-100 (warmed to 37° C.), 0.5% m/v cardiolipin in methanol, and DMSO/DMF substrate stock (warmed to 37° C.) respectively. For DBS assays, 40 mL of rehydrated blood mixture (from a DBS punch re-suspended in 200 mL of H$_2$O for 1 hr at RT with orbital shaking) was added to 10 mL of either H$_2$O or 30 mM aqueous Lalistat-2 solution (freshly prepared from a 0.3 mM DMSO stock) were pre-incubated for 10 min at 37° C. in a black, 96-well microtiter plate. Assay cocktail (100 or 150 mL) was added, and samples were incubated at 37° C. for 3 hrs. For recombinant-LAL, assays, 2 mL of enzyme solutions at various concentrations (from serial dilutions of a 2 mg/mL stock stored at 4° C.) were added to 10 mL of H$_2$O or 30 mM Lalistat-2 solution and incubated at RT for 10 min with 200 rpm of orbital shaking. The process was then same as the DBS version. The assay was quenched by addition of 100 mL of H$_2$O. Samples were immediately read on a plate-reader fluorometer with an excitation wavelength of 355 nm and emission wavelength of 460 nm. The fluorometric calibration curve was established using the same procedure as above using rehydrated base pool blood (blood devoid of leukocytes) except for the addition of 8 mL of H$_2$O and 2 mL of 4-MU standard solution (ranging from 0-2.5 nmol).

Testing the Library of Palmiotyl-4MU Analogs with LAL

FIG. 5 shows the structures of palmitoyl-4MU analogs (Compounds 1 and 14-37) tested as LAL substrates. These were prepared using the general synthetic scheme (described above). The coumarin (4MU) analogs shown in FIG. 5, from which the palmitoyl-4MU analogs prepared, were obtained from the indicated commercial sources.

The library of palmitoyl-4MU analogs was tested as LAL substrates as follows. Assay cocktail was a solution of 10:1 buffer to substrate stock, each warmed to 37° C. The substrate stock contained 3.7 mM substrate and 0.5% cardiolipin in ethanol. The buffer contained 0.15 M sodium acetate, pH 4.0, and 2.5 mM sodium taurodeoxycholate. Rehydrated blood mixture (40 mL) was combined with 10 mL of H$_2$O or 30 mM Lalistat-2 in an Eppendorf 1.5 mL polypropylene tube and pre-incubated for 15 min at 37° C. with orbital shaking at 250 rpm. Assay cocktail (100 or 150 mL) was added and samples were incubated for 3 hr at 37° C. with orbital shaking at 250 rpm. Assay was quenched by first flash freezing to −80° C. followed by subsequent addition of 400 mL of ethyl acetate and thawing. Samples were then vortexed and centrifuged at 2700×g for 5 min. Top ethyl acetate layer (200 mL) was transferred to an autosampler plate and blown dry under nitrogen gas then resuspended in 1:1 H$_2$O:methanol solution, and 10 mL per well injected for analysis by UPLC-MS/MS. The LC-MS/MS data was converted into mmole of product by using an external standard of 2.5 nmole (the individual corresponding coumarins) spiked into 40 mL rehydrated blood in a 1.5 mL Eppendorf polypropylene tube incubated separately from the assay cocktail, which were quenched immediately following incubation. Additional controls included a Lalistat-2 inhibited rehydrated DBS solution incubated separately from the assay cocktail then combined and immediately quenched as a blank. Unique duplicate spiked controls and blank controls were used for each coumarin analog.

Compounds 14, 16, 17, 18, 21, 23, 24, 25, 29, 30, 34, 35, 36, and 37 were poor substrates with DBS as the source of LAL compared to palmitoyl-4MU and were not studied further. Compounds 15, 19, 20, 22, 28, 31, 32, and 33 showed higher activity but where poorly LAL-specific based on the observation that addition of Lalistat-2 did not substantially reduced the activity more than what was seen for palmitoyl-4MU. This left three compounds: Compounds 1, 26, and 27. Both Compounds 1 and 26 displayed greater than 90% of the LAL-specific activity measured with palmitoyl-4MU. Compound 1 was found to be more active than palmitoyl-4MU and thus it was pursued due to the highest combination of total lipase activity and LAL-specificity (see text herein for studies of its LAL specificity). The final optimized protocol for LAL assays using Substrate 1 is described above.

Studies with Patient DBS

LAL activity of Compound 1 (i.e., Substrate 1) measured with by UPLC-MS/MS. The results are summarized in FIG. 6.

While illustrative embodiments have been illustrated and described, it will be appreciated that various changes can be made therein without departing from the spirit and scope of the invention.

The invention claimed is:

1. A compound having formula (I):

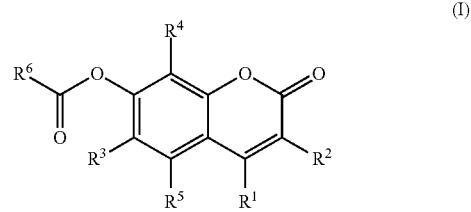

wherein

R$^1$ is linear or branched C1-C6 alkyl, optionally wherein one of the carbon atoms is replaced with an oxygen atom, R$^2$ is selected from the group consisting of (a) hydrogen and (b) linear or branched C1-C6 alkyl, optionally wherein one of the carbon atoms is replaced with an oxygen atom R$^3$ is selected from the group consisting of (a) hydrogen and (b) linear or branched C1-C6 alkyl, optionally wherein one of the carbon atoms is replaced with an oxygen atom R$^4$ is a linear or branched C1-C6 alkyl, optionally wherein one of the carbon atoms is replaced with an oxygen atom;

R$^5$ is hydrogen; and

R$^6$ is a linear or branched C5-C17 alkyl or alkenyl group, optionally wherein one, two, or three of the carbon atoms are replaced with an oxygen atom, wherein the alkenyl group includes one, two, three or four carbon-carbon double bonds, and wherein the alkyl or alkenyl group is optionally substituted with a phenyl group.

2. The compound of claim 1, wherein $R^6$ is $CH_3-(CH_2)n-$, wherein n is an integer from 4 to 16.

3. The compound of claim 2, wherein n is 14.

4. The compound of claim 2, wherein $R^1$ is propyl, $R^2$ and $R^3$ are hydrogen, and $R^4$ is methyl.

5. A method for assaying lysosomal acid lipase, comprising:
    (a) contacting a sample with a first solution to provide a first solution comprising lysosomal acid lipase;
    (b) contacting the first solution comprising lysosomal acid lipase with a compound of claim 1 and incubating the compound with the enzyme for a time sufficient to provide a solution comprising a lysosomal acid lipase enzyme product; and
    (c) determining the quantity of the lysosomal acid lipase enzyme product.

6. The method of claim 5, wherein the quantity of the lysosomal acid lipase enzyme product is determined by mass spectrometric analysis or fluorometric analysis.

7. The method of claim 5, wherein the sample is whole blood, serum, plasma, or a lysate.

8. The method of claim 5, wherein the sample is a dried blood spot.

9. The method of claim 5, wherein the substrate is 4-propyl-7-palmitoyloxy-8-methylcoumarin.

10. The method of claim 5 further comprising contacting the first solution with a phospholipid prior to incubation.

11. The method of claim 5 further comprising contacting the first solution with an internal standard prior to incubation.

12. The method of claim 11, wherein the internal standard is an isotopically labeled lysosomal acid lipase enzyme product.

13. The method of claim 5, wherein the quantity of the lysosomal acid lipase enzyme product is determined by mass spectrometric analysis.

14. The method of claim 5, wherein the quantity of the lysosomal acid lipase enzyme product is determined by tandem mass spectrometry (MS/MS).

15. The method of claim 5, wherein the quantity of the lysosomal acid lipase enzyme product is determined by fluorometric analysis.

16. The method of claim 5 further comprising using the quantity of the lysosomal acid lipase enzyme product to determine whether the sample is from a candidate for treatment of a condition associated with lysosomal acid lipase deficiency.

17. The method of claim 16, wherein the condition is Wolman disease or cholesterol ester storage disease.

18. The method of claim 5, wherein the method is a newborn screening assay.

19. A compound having formula (I):

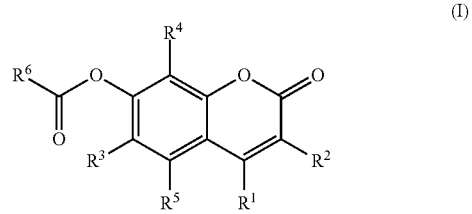

(I)

wherein
$R^1$ is n-propyl,
$R^2$ is hydrogen,
$R^3$ is hydrogen,
$R^4$ is methyl,
$R^5$ is hydrogen, and
$R^6$ is $-(CH_2)_{14}-CH_3$.

20. A method for assaying lysosomal acid lipase, comprising:
    (a) contacting a sample with a first solution to provide a first solution comprising lysosomal acid lipase;
    (b) contacting the first solution comprising lysosomal acid lipase with the compound of claim 19 and incubating the compound with the enzyme for a time sufficient to provide a solution comprising a lysosomal acid lipase enzyme product; and
    (c) determining the quantity of the lysosomal acid lipase enzyme product.

* * * * *